(12) United States Patent
Majeti et al.

(10) Patent No.: US 9,403,869 B2
(45) Date of Patent: Aug. 2, 2016

(54) $\alpha_5\beta_1$ INTEGRIN BINDING RGD-LIPOPEPTIDES WITH GENE TRANSFER ACTIVITIES

(75) Inventors: Bharat Kumar Majeti, La Jolla, CA (US); Priya Prakash Karmali, La Jolla, CA (US); Pramanik Dipankar, Andhra Pradesh (IN); Arabinda Chaudhuri, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 1715 days.

(21) Appl. No.: 12/295,107

(22) PCT Filed: Mar. 30, 2007

(86) PCT No.: PCT/IB2007/000826
§ 371 (c)(1),
(2), (4) Date: Jun. 2, 2010

(87) PCT Pub. No.: WO2007/116276
PCT Pub. Date: Oct. 18, 2007

(65) Prior Publication Data
US 2010/0234289 A1 Sep. 16, 2010

(30) Foreign Application Priority Data
Mar. 31, 2006 (IN) .......................... 0924/DEL/2006

(51) Int. Cl.
| A61K 38/16 | (2006.01) |
| A61K 5/11 | (2006.01) |
| A61K 31/711 | (2006.01) |
| A61K 31/7105 | (2006.01) |
| A61P 35/00 | (2006.01) |
| A61K 38/00 | (2006.01) |
| A61K 48/00 | (2006.01) |

(52) U.S. Cl.
CPC ............ *C07K 5/1019* (2013.01); *A61K 48/0008* (2013.01); *A61K 38/00* (2013.01); *A61K 48/00* (2013.01)

(58) Field of Classification Search
CPC . C07K 5/1019; A61K 48/00; A61K 48/0008; A61K 38/00
See application file for complete search history.

(56) References Cited

U.S. PATENT DOCUMENTS 6,083,741 A * 7/2000 Hart et al. ................. 435/320.1
6,346,516 B1 * 2/2002 Banerjee et al. ............ 514/44 R

FOREIGN PATENT DOCUMENTS

EP 0488258 A2 6/1992

OTHER PUBLICATIONS

Stepanenko et al, Journal of Bioorganic Chemistry, V.30, No. 2, 2004, p. 111.*
Harmali J Med Chem 2004 p. 2123.*
Vogel, A novel Integrin, Journal of Cell Biology 1993 p. 462.*
Xiao-Bing Xiong et al.; "Enhanced Intracellular Uptake of Sterically Stabilized Liposomal Doxorubicin in Vitro Resulting in Improved Antitumor Activity in Vivo"; Pharma.Res, vol. 22, No. 6; p. 933-939; Jun. 2005.
Pascale Belguise-Vallandier et al.; "Nonviral Gene Delivery: Towards Artificial Viruses"; Cytotechnology, vol. 35, p. 197-201, 2001.
Harbottle R P et al.; "An RDG-Oligolysine Peptide: A Prototype Construct for Integrin-Mediated Gene Delivery"; Human Gene Therapy vol. 9:1037-1047; May 1, 1998.

* cited by examiner

*Primary Examiner* — Suzanne Ziska
*Assistant Examiner* — Thurman Wheeler
(74) *Attorney, Agent, or Firm* — Harness, Dickey & Pierce, PLC

(57) ABSTRACT

The present invention provides synthesis of a novel series of cationic lipopeptides with integrin-binding RGD functionalities. The invention also provides high L27 (transformed S1 80, mouse sarcoma cells) cell tropic gene transfer properties of these novel RGD-lipopeptides. Since L27 cell surface contains over expressed integrins, the present class of lipopeptides with integrin-binding RGD ligands are likely to find future applications in targeting anti-cancer genes/drugs to the endothelial cells of tumor vasculatures (possessing over expressed integrins).

13 Claims, 6 Drawing Sheets

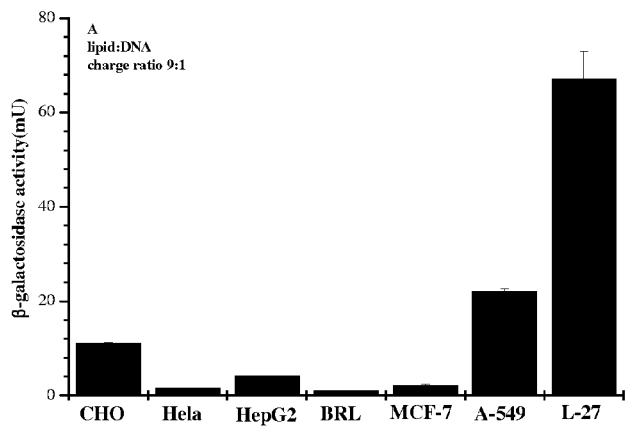
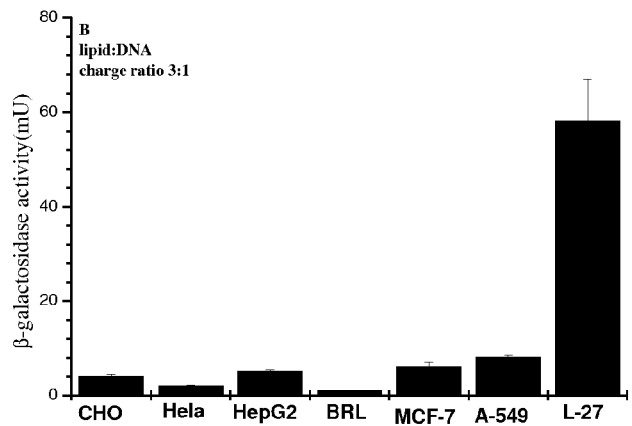
Figure 1: Part A and B- in vitro gene delivery efficacy profiles of RGD-lipopeptide in multiple cultured cells using lipoplexes with lipid:DNA Charge ratios 9:1 (A), 3:1 (B), 1:1 (C) and 0.3:1 (D).

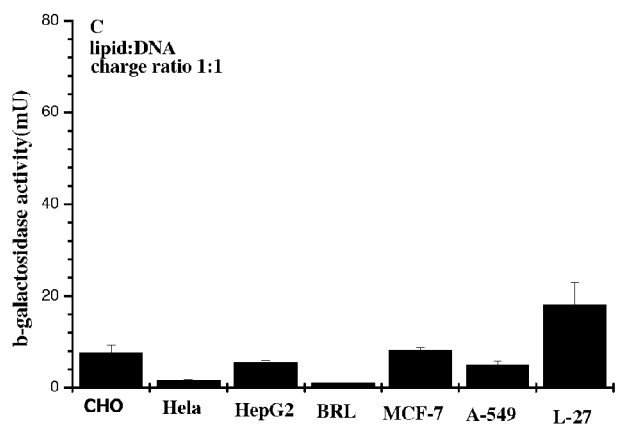
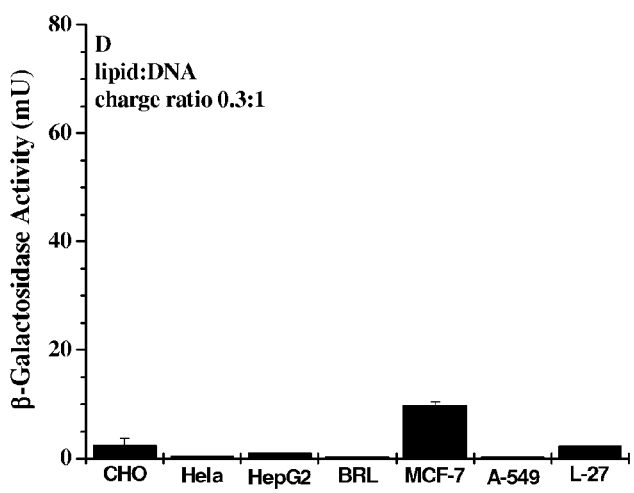
Figure 1: Part C and D- in vitro gene delivery efficacy profiles of RGD-lipopeptide in multiple cultured cells using lipoplexes with lipid:DNA Charge ratios 9:1 (A), 3:1 (B), 1:1 (C) and 0.3:1 (D).

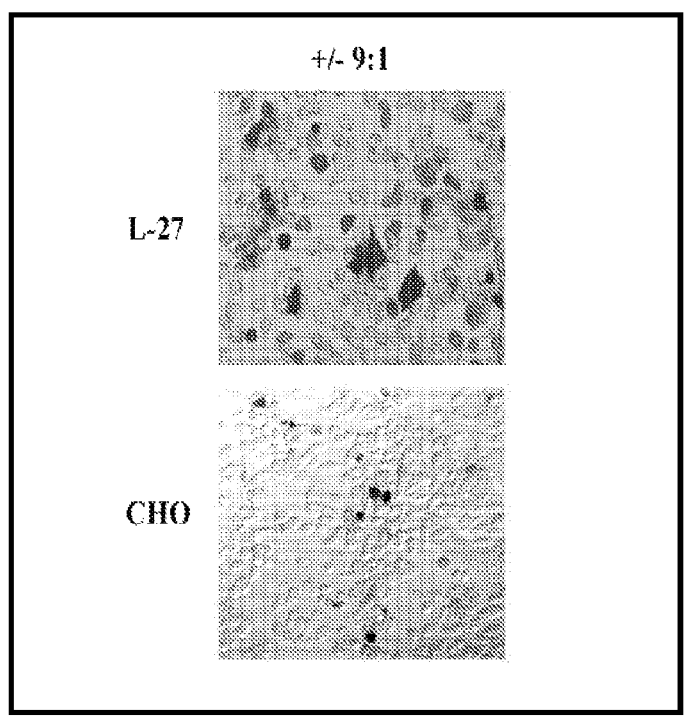
Figure 2: The whole cell histochemical X-gal staining profiles for RGD-lipopeptide in L27 and CHO cells using lipoplexes with lipid:DNA charge ratio 9:1.

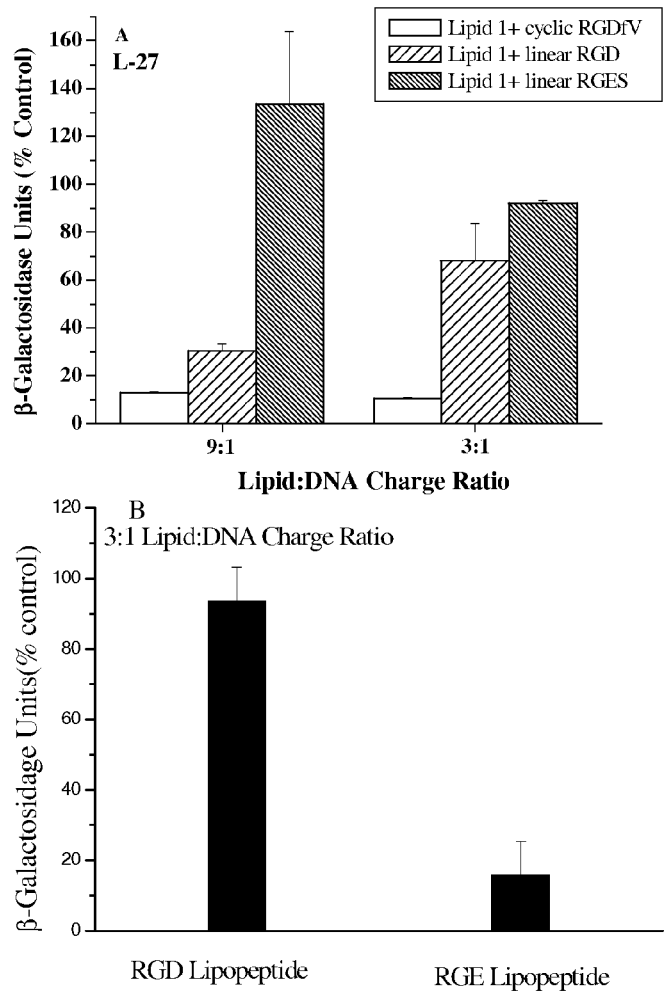
Figure 3: Part A summarizes the reduced gene transfer profiles and part B shows the comparison between transfer efficiencies of integrin and non integrin binding RGD lipopeptide in L27 cells pretreated with monoclonal antibodies against $\alpha 5\beta 1$, $\alpha v\beta 3$ and $\alpha v\beta 5$ integrin receptors.

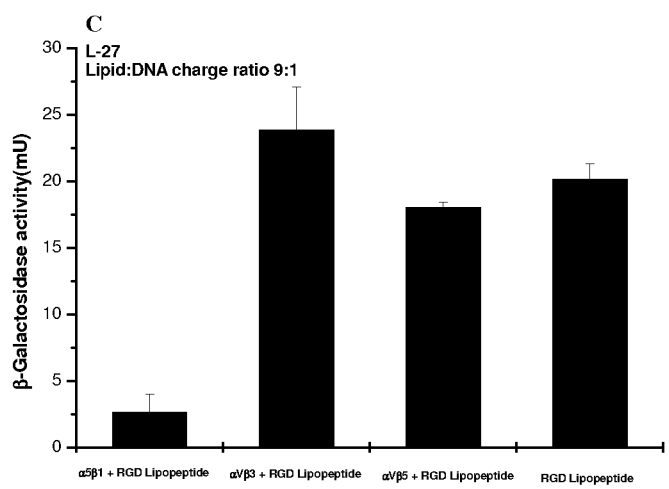
Figure 3: Part C depicts the relative gene transfer efficiencies of the RGD-lipopeptide in L27 cells pretreated with monoclonal antibodies against $\alpha_5\beta_1$, $\alpha_v\beta_3$ and $\alpha_v\beta_5$ integrin receptors.

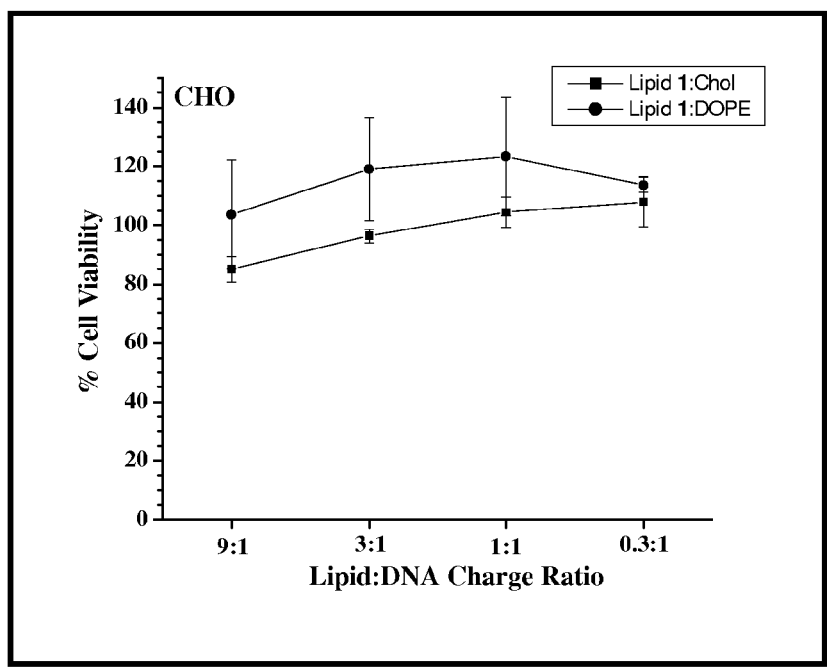
Figure 4: MTT-assay based in vitro cellular toxicity profiles for RGD-lipopetide in CHO cells

$\alpha_5\beta_1$ INTEGRIN BINDING RGD-LIPOPEPTIDES WITH GENE TRANSFER ACTIVITIES

FIELD OF THE INVENTION

The present invention relates to a novel series of cationic amphiphiles containing RGD-tripeptide ligands of the $\alpha_5\beta_1$ integrin-receptors and methods for preparing. The invention provides novel compositions containing the said amphiphiles with remarkable gene transfer properties. The area of medical science that is likely to benefit most from the present invention is non-viral cancer gene therapy.

BACKGROUND AND PRIOR ART INFORMATION

Angiogenesis (also called neovascularization), the formation and differentiation of blood vessels from pre-existing vessels or endothelial progenitor cells, is important in both health and disease. Angiogenesis occurs normally during embryogenesis and development, and occurs in fully developed organisms during wound healing and placental development. In addition, angiogenesis occurs in various pathological conditions such as diabetic retinopathy and macular degeneration due to neovascularization, rheumatoid arthritis, inflammatory bowl disease and in cancer, where the newly formed blood vessels supply oxygen and nutrients to the growing tumor. Endothelial cells lining the mature blood vessels normally do not proliferate. During vascular remodeling and angiogenesis, endothelial cells show increased expression of cell surface molecules that potentiate cell invasion and proliferation. Integrins, the super family of heterodimeric membrane bound proteins consisting of several different alpha and beta subunits, are one such class of several cell surface molecules which are up regulated in the proliferating endothelial cells of the tumor vasculature and are also found on different tumor cells including metastatic melanoma cells.

Integrins are important for attachment of cells to the extracellular matrix; cell-cell interactions and signal transduction. A large number of pathogens including *Typanosoma cruzi*, adenovirus, echovirus, foot-and-mouth disease virus as well as the enteropathogen *Y. pseudotuberculosis* pathogens exploit integrin receptors for entering our body cells. A distinguished advantage of the integrin-mediated internalization process is that it proceeds by a phagocytic-like process allowing internalization of relatively large structures such as pathogenic bacteria with diameters as big as one to two micrometers. In other words, integrin-specific targeting of non-viral vectors holds potential in avoiding the lower size limitation imposed by the clathrin-coated vesicles commonly involved in many other receptor-mediated endocytosis. Interestingly, the amino acid sequence arginine-glycine-aspartic acid (RGD) is the most evolutionary conserved feature of many, but not all, natural integrin-binding ligands such as extracellular matrix proteins and viral capsids. Because of their high integrin-receptor affinities, cyclic peptides containing RGD domains have been found to be particularly suitable as integrin-targeting vectors. This is why RGD-ligand mediated targeting of anti-cancer genes/drugs to the integrin receptors over expressed on the endothelial cell surfaces of tumor vasculatures (rather than targeting the tumor cells themselves) is a promising anti-angiogenic approach to combat cancer. To this end, the present invention relates to development of a novel series of simple RGD-lipopeptides with remarkably selective efficacies for delivering genes to cells containing over expressed integrin receptors.

A large number of integrin receptor targeting linear and cyclic peptide ligands have been reported including sequences derived from natural protein ligands or sequences selected from phage display libraries (Pasqualini et al. Nature Biotechnology 1997; 15; 542-546, Wickham et al. J. Virology 1997; 71; 8221-8229, Arap et al. Science 1998; 279; 377-380, Erbacher et al. Gene Ther 1999; 6; 138-145, DeNardo et al. Cancer Biother. Radiopharm 2000; 15; 71-79, Müller et al. Cancer Gene Ther 2001; 8; 107-117, Janssen et al. Cancer Res 2002; 62; 6146-6151, Schraa, et al. Int. J. Cancer 2002; 102; 469-475). One of the most potent RGD peptides (RGD4C; CDCRGDCFC) is composed of a central RGD motif structurally stabilized by two disulfide bonds (Koivunen et al. Biotechnology 1995; 13; 265-270). Previously, Hart et al. demonstrated that multiple copies of a cyclic RGD-peptides displayed in the major coat protein subunit of fd filamentous phage particles, approximately 900 nm in length, are internalized efficiently by cells in tissue culture in an integrin-mediated manner (Hart et al. J. Biol. Chem. 1994; 269; 12468-12474). Hart et al. also succeeded in exploiting poly-lysinated peptides covalently linked to multiple RGD-peptides for ensuring integrin-mediated gene expression in epithelial cell lines (Hart et al. Gene Ther 1995; 2; 552-554, 1996, WO96/15811). More recently, Hart et al. disclosed that inclusion of a lipid component in the oligolysine/RGD-peptide/DNA complex remarkably improves levels of gene transfection (U.S. Pat. No. 6,458,026, Hart et al. 2002). Very recently, using phage display technology, Holig et al. (Holig, P. et al. Prot. Eng. Design & Selection, 2005; 17; 433-441) has succeeded in isolating a series of novel RGD-lipopeptides which upon incorporation into liposomes exhibited specific and efficient binding to integrin-expressing cells.

Anticancer drug developments have mostly been centered around designing selective antagonists of $\alpha_v\beta_3$ and $\alpha_v\beta_5$ integrins (Richard O. Hynes. Nature Med 2002; 8; 918-921, Brooks et al. Science 1994; 264; 569-571, Brooks et al. Cell 1994; 79; 1157-1164, Brooks et al. J. Clin. Invest. 1995; 96; 1815-1822; Friedlander et al. Science 1995; 270; 1500-1502, Friedlander et al. Proc. Natl. Acad. Sci. USA 1996; 93; 9764-9769; Hammes et al. Nature Med 1996; 2; 529-533). However, it has been demonstrated that mice lacking one or both of the $\alpha_v\beta_3$ and $\alpha_v\beta_5$ integrins show enhanced tumor growth and extensive angiogenesis (Reynolds et al. Nature Med. 2002; 8; 27-34, Bader et al. Cell 1998; 95; 507-519). Among the 24 different integrin receptors, the fibronectin receptor $\alpha_5\beta_1$ appears to be the most unambiguous, proangiogenic integrin receptor (Anne et al. Cancer Research 2006; 66; 6002-6007, Curley et al. Cell Mol. Life Sci. 1999; 56; 427-441, Francis et al. Arterioscler Thromb Vasc Biol 2002; 22; 927-933). $\alpha_5\beta_1$ integrin receptors are overexpressed in angiogenic endothelial cells and therefore, are likely to represent a new target in antiangiogenic cancer therapy (Kita et al. Cancer Research 2001; 61; 7985-7991). Designs on sterically stealth liposomes containing covalently grafted RGD-functionalities (Xiao-Bing Xiong et al. Pharmaceutical Research 2005; 22; 933-939) and cationic polymer based non-viral gene delivery systems containing RGD-functionalities (Pascale Belguise-Valladier et al. Cytotechnology 2001; 35; 197-201) have been reported previously. However, none of these priorly reported gene transfer reagents exhibited any $\alpha_5\beta_1$ integrin receptor specificity. To this end, the present invention relates to development of a novel series of simple RGD-lipopeptides for $\alpha_5\beta_1$ integrin receptor mediated delivery of genes/drugs.

The present invention relates to development of a novel series of lipopeptides containing integrin-binding simple RGD tripeptide functionalities. The gene transfer properties of this new class of RGD-lipopeptide described herein is remarkably cell tropic for transformed mouse sarcoma cells (L27 cells). The gene transfer efficacies of the RGD-lipopeptides disclosed herein are significantly inhibited when cells are pre-incubated with commercially available integrin-binding cyclic peptide (RGDfV) indicating that the gene transfer process is mediated through integrin receptors. Thus, the present class of RGD-lipopeptides is likely to find future applications in anti-angiogenic cancer therapy for targeting anti-cancer genes/drugs to tumor vasculatures with over expressed integrin receptors.

OBJECT OF INVENTION

The object of present invention is to provide cationic lipopeptides based gene transfer reagents containing $\alpha_5\beta_1$ integrin-binding RGD head-groups and a method of preparation thereof.

SUMMARY OF THE INVENTION

Accordingly the present invention relates to a series of novel cationic RGD-lipopeptides and process for the synthesis and evaluation of their $\alpha_5\beta_1$ integrin-mediated gene transfer properties in various cultured animal cells.

The said cationic RGD-lipopeptide is represented by general formula A,

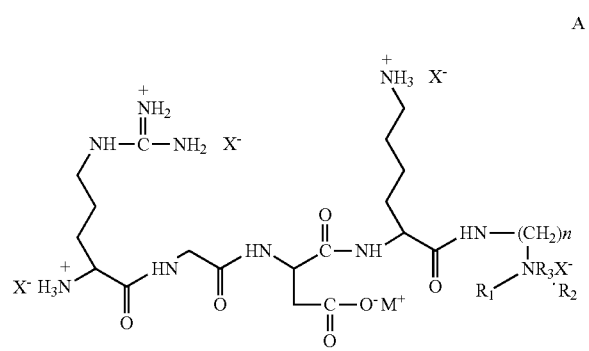

A wherein
each of $R^1$ and $R^2$ is independently hydrogen or a lipophilic moiety containing at least eight carbon atoms and is optionally selected from 8-22 carbon containing alkyl, mono-, di- and tri-unsaturated alkenyl ($C_8$-$C_{22}$) provided both R' and $R^2$ are not hydrogen;
$R^3$ is independently hydrogen or alkyl ($C_1$-$C_5$, straight or branched);
n is an integer between 1 and 7;
X is optionally a halogen moiety;
and
M is selected from the group comprising hydrogen, sodium and potassium atom.

In another embodiment of the invention the disclosed cationic lipids $R_1$=$R_2$=n-hexadecyl, $R_3$ is a proton, n=2, M is a sodium atom and $X^-$ is a chloride ion the amphiphile no. 1

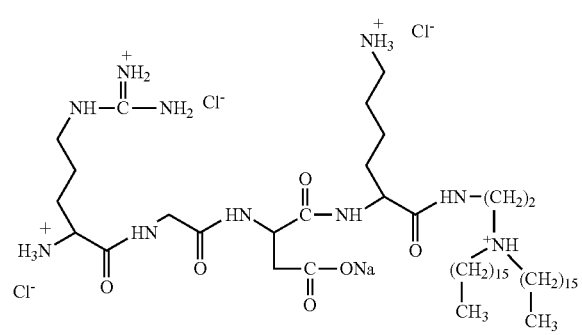

1

In still another embodiment of the invention, the RGD-lipopeptide complex has each of $R_1$ and $R_2$ is independently hydrogen or an aliphatic hydrocarbon chain.

In yet another embodiment of the invention, the RGD-lipopeptide complex has both $R_1$ and $R_2$ as aliphatic hydrocarbon chains.

In an embodiment of the invention, the RGD-lipopeptide complex in which $R_3$ is an alkyl group and both $R_1$ and $R_2$ are aliphatic hydrocarbon chains.

In another embodiment of the invention, the RGD-lipopeptide complex where $R_3$ is a hydrogen atom and both $R_1$ and $R_2$ are aliphatic hydrocarbon chains.

In still another embodiment of the invention, the RGD-lipopeptide complex where $R_3$ is an alkyl group and $R_1$ and $R_2$ are independently hydrogen or an aliphatic hydrocarbon chain.

In yet another embodiment of the invention, the RGD-lipopeptide complex where each one of $R_1$ and $R_2$ groups containing about 8-22 carbon atoms is independently alkyl group containing 8-22 carbon atoms or a mono-, di- or tri-unsaturated alkenyl group containing 8-22 carbon atoms.

In an embodiment of the invention, the RGD-lipopeptide complex where each group containing about 16 to about 22 linked carbon atoms is independently a mono-unsaturated alkenyl (C.sub.16-22) group.

In another embodiment of the invention, the RGD-lipopeptide complex where both $R_1$ and $R_2$ are the same and saturated alkyl group containing 12-18 carbon atoms.

In still another embodiment of the invention, the RGD-lipopeptide complex where both $R_1$ and $R_2$ are the same and are mono-unsaturated alkenyl group containing 18-22 carbon atoms.

In yet another embodiment of the invention, the RGD-lipopeptide complex where X is selected from the halogen group.

In yet another embodiment of the invention, X is selected from the group comprising chlorine, bromine and iodine.

In an embodiment of the invention, a formulation comprising a RGD-lipopeptide represented by generic structure A along with one or more polyanionic compound and one or more physiologically acceptable additives.

In one more embodiment of the invention the said formulation further comprises co lipid.

In another embodiment of the invention, the formulation where the RGD lipopeptides is used in pure form or in combination with co lipids.

In still another embodiment of the invention, the formulation where the helper lipid is selected from the group comprising of phosphatidylethanolamine, phosphatidylglycerol, cholesterol.

In an embodiment of the invention, the formulation where the colipid is selected from sterol group or a neutral phosphatidyl ethanolamine or a neutral phosphatidyl choline.

In another embodiment of the invention, the formulation, where the colipid is preferentially selected from DOPE or cholesterol In still another embodiment of the invention, the formulation, where the range of molar ratio of RGD lipopeptide to colipid is 3:1-1:1.

In yet another embodiment of the invention, the formulation, where in the preferred molar ratio of RGD lipopeptide to colipid is 1:1.

In an embodiment of the invention, the formulation where the a polyanionic compound is selected from a group of nucleic acid that encodes for a therapeutically important protein, nucleic acid, an oligonucleotide, a peptide or a protein and drug.

In another embodiment of the invention, the formulation where the nucleic acid is selected from the group of a circular or linear plasmid or is a ribonucleic acid, a ribosomal RNA, antisense polynucleotide of RNA, antisense polynucleotide of DNA, polynucleotide of genomic DNA, cDNA or mRNA In still another embodiment of the invention, the formulation where the polyanion is used singly or in combination.

In yet another embodiment of the invention, the formulation where the said formulation is administered intravenously, intramuscularly or in intraperitonial mode.

In another embodiment of the invention, the formulation where the said formulation is administered to cells at a ratio 0.1 to 0.5 microgram of DNA to 50,000 cells In still another embodiment of the invention, the formulation where the said formulation comprises amount of amphiphile in the range of 9.0 to 0.3 microgram from a lipopeptide to DNA charge ratio ranging from 0.3:1 to 9:1

In yet another embodiment of the invention, a transfection complex comprising of the formulation.

An embodiment of the invention is evaluation of endothelial cell specific gene delivery properties of the new RGD-lipopeptide represented by the above-mentioned structure A.

BRIEF DESCRIPTION OF DRAWINGS

FIG. 1 (Parts A-D) summarizes the in vitro gene delivery efficacy profiles for the RGD-lipopeptide 1 disclosed in the present invention in multiple cultured cells including CHO, MCF-7, A549, HepG2, HeLa, BRL and L27 cells across the lipopeptide:DNA charge ratios of 9:1-0.3:1.

FIG. 2 shows the whole cell histochemical X-gal staining profiles of transfected CHO and L27 cells with the RGD-lipopeptide 1 at lipid:DNA charge ratios at 9:1.

Part A of FIG. 3 summarizes the reduced gene transfer profiles of the RGD-lipopeptide 1 in L27 cells when the cells are pre-incubated with the commercially available integrin antagonists such cyclic RGDfV and linear RGD tripeptides as well as with commercially available non-integrin ligand RGE. Part B of FIG. 3 shows that integrin-binding RGD-lipopeptide 1 possesses remarkably superior gene transfer properties to the non-integrin binding RGE-lipopeptide 2 in L27 cells. Part C of FIG. 3 shows that the cellular uptake of the RGD-lipopeptide 1:DNA complex is mediated through $\alpha_5\beta_1$ integrin receptors.

FIG. 4 depicts the in vitro cellular toxicity profiles for RGD-lipopeptide 1 used in combination with both DOPE and cholesterol as co-lipids across the lipopeptide:DNA charge ratios of 9:1-0.3:1.

DETAILED DESCRIPTION OF THE INVENTION

The present invention relates to a series of novel cationic RGD-lipopeptides. The novel cationic amphiphiles containing polar RGD-head groups are potentially useful to deliver anti-cancer genes/drugs into tumor vasculatures containing over expressed integrins. The area of science that is likely to be benefited most from the present invention is anti-angiogenic cancer therapy.

The distinctive novel structural features common to the cationic amphiphiles disclosed in the present invention include: (1) The presence of hydrophobic groups which are directly linked to the positively charged nitrogen atom and (2) the presence of integrin-binding polar arginine-glycine-aspartic acid-head-group. It is believed that these unique structural features contribute significantly to the integrin-mediated gene transfer efficiencies of the novel RGD-lipopeptides disclosed herein.

According to the practice of the present invention, "cationic" means the positive charge is either on quaternized nitrogen or on a protonated nitrogen atom. The cationic characters of the present amphiphiles may contribute to the enhanced interaction of the amphiphiles with biologically active molecules such as nucleic acids and/or with cell constituents such as plasma membrane glycoproteins. Such enhanced interaction between the cationic amphiphiles and therapeutically active biological macromolecules and/or cell membrane constituents may play a key role in successfully transporting the therapeutic molecules into the cells.

The cationic RGD-lipopeptide of the present invention has certain common structural and functional groups. As such, the said cationic RGD-lipopeptide may be represented by the following generic formula (A):

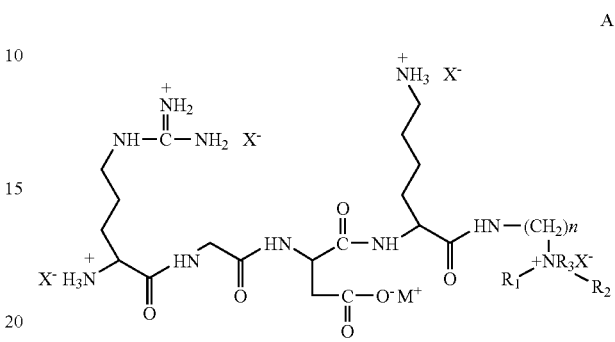

A wherein
each of $R^1$ and $R^2$ is independently hydrogen or a lipophilic moiety containing at least eight carbon atoms and is optionally selected from 8-22 carbon containing alkyl, mono-, di- and tri-unsaturated alkenyl ($C_8$-$C_{22}$) provided both $R^1$ and $R^2$ are not hydrogen;
$R^3$ is independently hydrogen or alkyl ($C_1$-$C_5$, straight or branched);
n is an integer between 1 and 7;
M is selected from the group comprising hydrogen, sodium and potassium atom; and
X is optionally a halogen moiety.

The RGD-lipopeptides of the present invention have a lipophilic domain that facilitates the formation of lipid complexes or aggregates in aqueous solutions. The lipophilicity of the hydrophobic domains and the hydrophilicity of the polar RGD-head group domains are such that when the cationic lipids are confronted with aqueous solutions, lipid aggregates are formed in the presence or absence of a second compound. Exemplary lipophilic $R_1$ and $R_2$ groups include (1) saturated $C_8$-$C_{22}$ alkyl groups and (2) unsaturated $C_8$-$C_{22}$ alkenyl groups containing 1, 2, or 3 double bonds.

In one preferred embodiment of the presently disclosed cationic lipids $R_1$=$R_2$=n-hexadecyl, $R_3$ is a proton, n=2, M is a sodium atom and $X^-$ is a chloride ion. Accordingly, the amphiphile no. 1 is a representative example of the presently described novel RGD-lipopeptide:

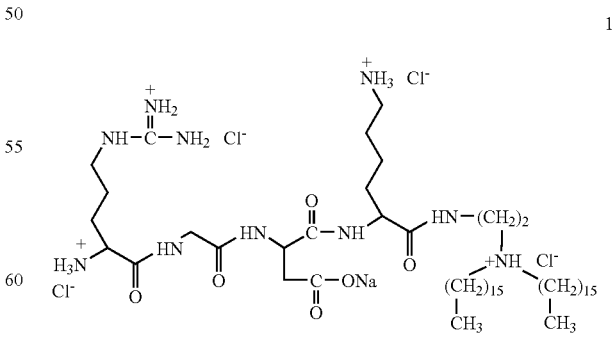

1

The present invention also relates to process for the synthesis of a series of novel cationic RGD-lipopeptides and evaluation of their integrin-mediated gene transfer properties in various cultured animal cells.

Synthesis of the Cationic Lipids
Scheme 1
Scheme 1 outlines the synthetic strategy employed for preparing the representative integrin-binding RGD-lipopeptide 2 described in the present invention.
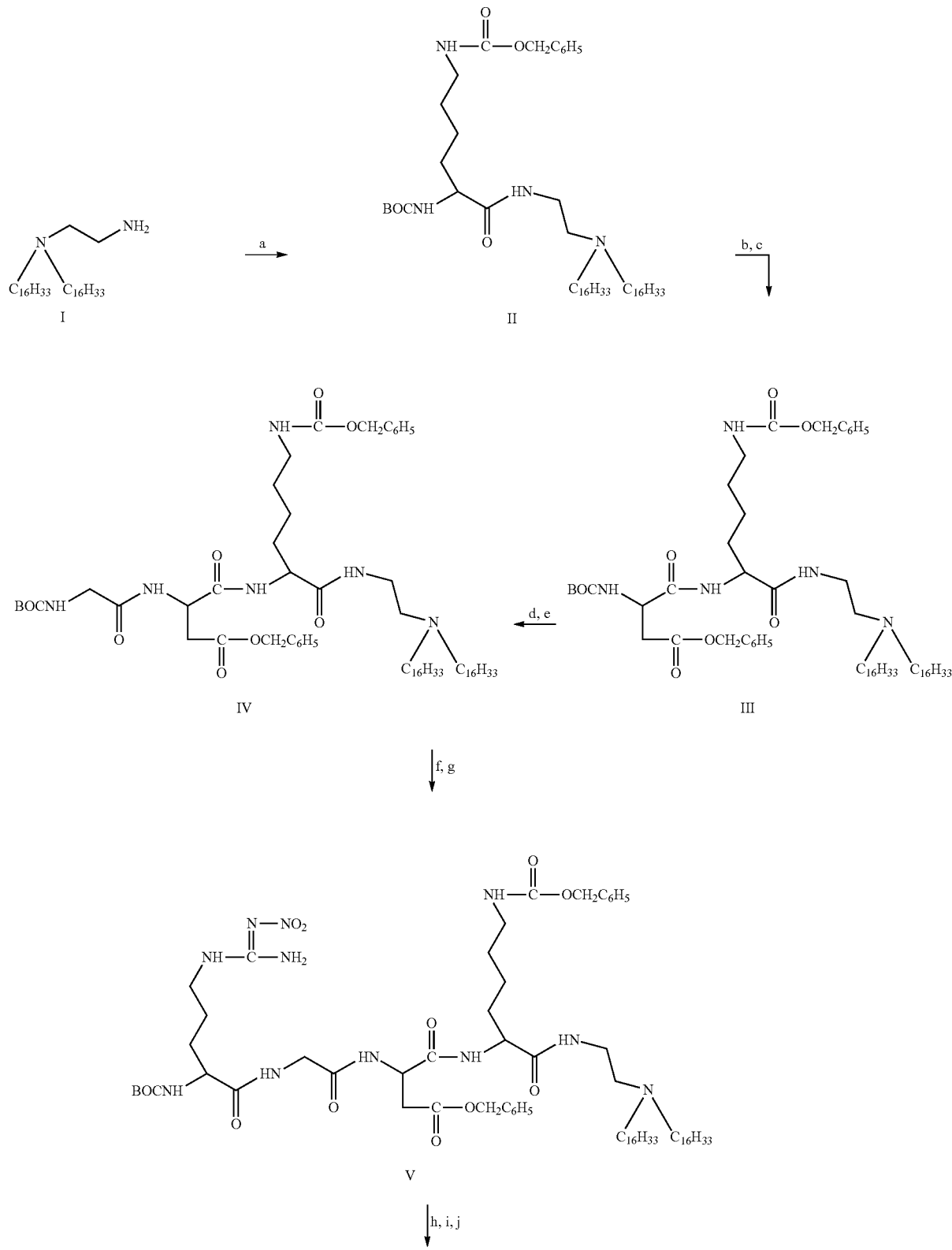

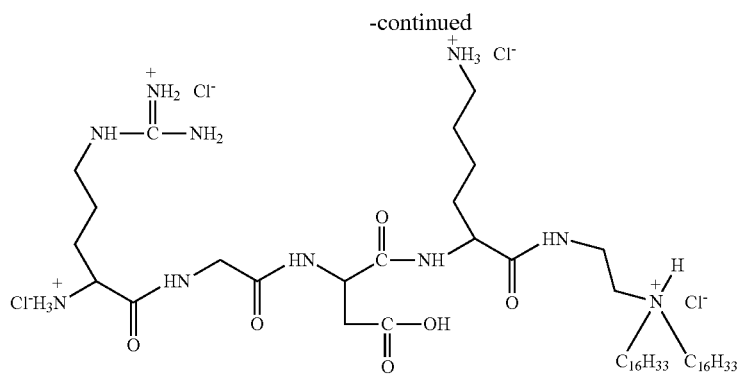

2

Reagents: (a) BOCLys(Z)OH, DCC, HOSu, DMAP; (b) DCM; TFA (c) BOCAsp(Bz)OH, DCC, HOSu, DMAP; (d) TFA, DCM; (e) BOCGly OH, DCC, HOSu, DMAP; (f) TFA, DCM (g) BOCArg(NO$_2$)OH, DCC, HOSu, DMAP; (h) TFA, DCM; (i) H$_2$, 10% Pd/C; (j) Cl$^-$ ion exchange (A-26 Amberlyst resin).

The RGD-Lipopeptide 2 was synthesized by sequential DCC-coupling of N-2-aminoethyl-N,N-di-n-hexadecylamine with appropriately protected amino acid derivatives followed by acid deprotection, hydrogenation and chloride ion exchange chromatography as outlined in Scheme 1. Structures of all the synthetic intermediates and final lipids shown in Scheme 1 were confirmed by $^1$H NMR. The final lipids were further characterized by the molecular ion peaks in their LSIMS. Purity of lipid 2 was confirmed by reverse phase analytical HPLC using two different mobile phases.

Formulations

The invention also provides novel formulation comprising optimal amounts of the cationic RGD-lipopeptide disclosed herein, biological macromolecules and the co-lipids. One or more additional physiologically acceptable substances may be included in the pharmaceutical formulation of the invention to stabilize the formulation for storage or to facilitate successful intracellular delivery of the biologically active molecules. Co-lipids according to the practice of the present invention are useful in mixing with one or more the RGD-lipopeptides. Cholesterol is an excellent co-lipid for use in combination with the presently described RGD-lipopeptides to facilitate successful intracellular delivery of the biologically active molecules. A preferred range of molar ratio of RGD-lipopeptide to co-lipid is 1:1. As such, it is within the art to vary the said range to a considerably wide extent. Typically, liposomes were prepared by dissolving the RGD-lipopeptide and the co-lipid (Cholesterol or DOPE) in the appropriate mole ratio in a mixture of methanol and chloroform in a glass vial. The solvent was removed with a thin flow of moisture free nitrogen gas and the dried lipid film was then kept under high vacuum for 8 h. The dried lipid film was hydrated in sterile deionized water in a total volume of 1 mL at RGD-lipopeptide concentration of 1 mM for a minimum of 12 h. Liposomes were vortexed for 1-2 minutes to remove any adhering lipid film and sonicated in a bath sonicator (ULTRAsonik 28x) for 2-3 minutes at room temperature to produce multilamellar vesicles (MLV). MLVs were then sonicated with a Ti-probe (using a Branson 450 sonifier at 100% duty cycle and 25 W output power) for 1-2 minutes to produce small unilamellar vesicles (SUVs) as indicated by the formation of a clear translucent solution.

Biologically active molecules that can be administered intracellularly in therapeutic amounts using the RGD-lipopeptides of the present invention include ribosomal RNA, antisense polynucleotide of RNA or DNA, polynucleotide of genomic DNA, cDNA or mRNA that encodes for a therapeutically important protein and anti-angiogenic genes/drugs. The RGD-lipopeptides of the present invention may be blended such that one or more of the representatives thereof may be used in a combination to facilitate entry of the said biologically active molecules into cells/tissues.

In a further embodiment, the RGD-lipopeptides disclosed in the present invention may be used either in pure form or in combination with other lipids or helper lipids such as cholesterol, phosphatidylethanolamine, phosphatidylglycerol, etc. The said therapeutic formulation may be stored at 0° C.-4° C. until complexed with the biologically active therapeutic molecules. Agents that prevent bacterial growth and increase the shelf life may be included along with reagents that stabilize the preparation, e.g., low concentrations of glycerol. It is specifically warned that freezing and thawing cycles could cause loss in efficiency of the formulation.

In yet another embodiment, the formulation of the RGD-lipopeptides disclosed herein, co-lipids (cholesterol or DOPE) and the biologically active therapeutic molecules may be administered intravenously besides other routes such as intramuscular and intraperitonial. Further, the said formulations may be administered to cells at a ratio of 0.1-0.5 microgram of DNA to 50,000 cells in an in vitro system. The amount of amphiphile could be varied from a lipopeptide to DNA charge ratio of 0.3:1 to 9:1 considering three positive charges for one RGD-lipopeptide molecule and one negative charge of a single nucleotide base.

The invention further provides a process for the preparation of the said formulation comprising the steps of preparing a dispersion of a RGD-lipopeptide disclosed in the present invention; contacting said dispersion with a biologically active molecule to form a complex between said RGD-lipopeptide and the said biologically active molecules and contacting the cells with the said complex thereby facilitating transfer of said biologically active molecules into the cells. The present invention also provides with various formulations that facilitate intracellular delivery of biologically active molecules.

$\alpha_5\beta_1$ Integrin-Receptor Specific Gene Delivery Properties of the Presently Described RGD-Lipopeptides:

The in vitro transfection efficacies of liposomes containing the RGD-lipopeptide A in combination with either cholesterol or DOPE as co-lipid at a mole ratio of 1:1 were evaluated by reporter gene expression assay using pCMV-SPORT-β-gal plasmid as the reporter gene in CHO, HeLa; HepG2, BRL, MCF-7, A549 and L-27 cells across the lipopeptide:DNA charge ratios 9:1-0.3:1. RGD-lipopeptide A was nearly 7-70 folds more efficient in transfecting L-27 cells (a mouse sarcoma cell line transformed to over express $\alpha_5\beta_1$ integrins on its surface) (FIG. 1, Parts A-D) in all the cell lines studied when formulated with cholesterol as a co-lipid. Cholesterol was found as the co-lipid of choice since the gene transfer efficacy of RGD-lipopeptide A was compromised by nearly 3-4 folds in L-27 cells when DOPE was used as a co-lipid RGD-lipopeptide A was most efficient in transfecting L-27 cells at lipopeptide:DNA charge ratios of 9:1 and 3:1 (FIG. 1, Parts A-D).

The transfection efficiency of A was nearly abolished at lower lipopeptide:DNA charge ratios viz, 1:1 and 0.3:1 in L-27 cells (FIG. 1, Parts C-D). Low levels of reporter gene expression were observed for A in the otherwise highly transfectable CHO cells across all the charge ratios studied (FIG. 1, Parts A-D). In HepG2 and MCF-7 cells too, A exhibited poor transfection efficiency (FIG. 1, Parts A-D). The gene transfer efficacies of A in HeLa and BRL cells were almost insignificant across the entire range of lipopeptide:DNA charge ratios (FIG. 1, Parts A-D). The moderate gene transfer efficiency in A549 cells at the high lipid:DNA charge ratio of 9:1 (FIG. 1, Part A) is likely to originate from the presence of α5β1 integrin receptors expressed in A549 cell surface. The contrastingly enhanced β-galactosidase reporter gene expression level observed in L-27 cells (FIG. 1, Parts A-B) strongly indicate that transfection of $\alpha_5\beta_1$ integrin over expressing L-27 cells by lipid A is likely to be mediated by the integrin-binding RGD functionality of A. The superior transfection efficacy of A in combination with equimolar, cholesterol as a co-lipid in L-27 cells was further confirmed by whole cell histochemical X-gal staining of L-27 and CHO cells at a lipid:DNA charge ratio of 3:1 (FIG. 2). The poor efficacies of lipid A in transfecting other cells including the highly transfectable CHO cells might result from the poor cellular uptake of RGD-lipopeptide:DNA complexes in these cells with much lower levels of integrin receptors in their cell surfaces than those in L-27 cells.

The efficacies of the RGD-lipopeptide A in transfecting integrin receptor containing L27 cells got severely compromised when the gene transfer experiments were carried out by treating the cells with the cyclic RGDfV-peptides, the commercially available efficient integrin antagonists (Part A, FIG. 3). Thus, the results summarized in part A of FIG. 3 finding provided strong evidence for the involvement of integrin receptors for the present class of RGD-lipopeptide based gene delivery reagents. The gene transfer efficacies of the RGD-lipopeptide A was reduced to a lesser extent when L27 cells were pre-incubated with the linear tripeptide RGD, another commercially available integrin-binding ligand with lesser integrin-binding affinity than the cyclic RGDfV ligand (FIG. 3, Part A). The gene transfer efficacies of lipopeptide A were not significantly affected when L27 cells were pre-treated with the commercially available linear tetrapeptide RGES, a non-substrate for integrin receptors (FIG. 3, Part A). Since ROD and not RGE peptides are ligands for integrin receptors, we also synthesized lipopeptide 3 the RGE-counterpart of the representative RGD-lipopeptide A, following exactly the same synthetic protocols as outlined in Scheme 1 for synthesis of the RGD-lipopeptide A. As shown in Part B of FIG. 3, RGE-lipopeptide 3 showed significantly reduced gene transfer efficacies in L27 cells (containing over expressed integrins on its cell surface). Thus, the transfection results summarized in Parts A and B of FIG. 3, taken together, provide convincing support for the involvement of integrin receptors in the cellular uptake of the presently described RGD-lipopeptides.

Finally, toward probing whether or not the presently described RGD-lipopeptides possess selectivity for any specific integrin receptors, we evaluated the efficiencies of the ROD-lipopeptide 1 in transfecting L27 cells pre-incubated with commercially available monoclonal antibodies against $\alpha_5\beta_1$, $\alpha_v\beta_3$ and $\alpha_v\beta_5$ integrin receptors. As depicted in part C of FIG. 3, the transfection efficiencies of the RGD-lipopeptide 1 were significantly affected only when cells were pretreated with the monoclonal antibodies against $\alpha_5\beta_1$ integrin receptor and not with monoclonal antibodies against the integrin receptors $\alpha_v\beta_3$ and $\alpha_v\beta_5$.

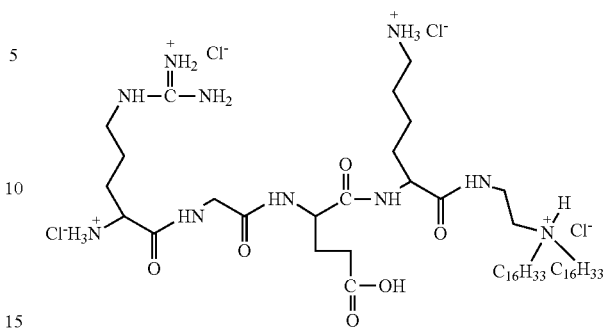

2

Cellular Cytotoxicities of the Amphiphiles Disclosed in the Invention

The cytotoxicities of the presently described RGD-lipopeptides in combination with both cholesterol and DOPE as co-lipids were assessed by MTT based cell viability assay as described previously (Majeti B. K. et al. J. Med. Chem. 2005; 46; 3784-3795). Both the formulations were found to be essentially non-toxic across the entire range of lipopeptide:DNA charge ratios of 9:1-0.3:1 (FIG. 4). Notably, both the formulations exhibited more than 80% cell viability even at higher lipid:DNA charge ratios (FIG. 4). Thus, the poor transfection efficiencies of the RGD-lipopeptide A in cells other than L-27 cells are unlikely to originate from any cellular toxicity related factors.

Applications:

The process of the present invention can be exploited for preparing cationic lipopeptides based gene transfer reagents containing integrin-binding RGD head-groups. The inventions of RGD-lipopeptides are useful for delivering polyanions, polypeptides or nucleopolymers into cells via $\alpha_5\beta_1$ integrin receptors. The cationic RGD-lipopeptides disclosed herein can be used to deliver an expression vector into a cell for manufacturing, or therapeutic use. The expression vectors can be used in gene therapy protocols to deliver a therapeutically useful protein to a cell or for delivering nucleic acids encoding therapeutically useful protein molecules. The invention RGD-lipopeptides can be formulated with anionic, zwitterionic and lipophilic therapeutic agents including anti-cancer agents such as doxorubicin, a lipophilic compound, to obtain complexes comprising the invention RGD-lipopeptides and a therapeutic agent(s). In particular, the presently disclosed RGD-lipopeptides hold potential for future exploitation in delivering anti-cancer genes/drugs to tumor vasculature, the anti-angiogenic therapeutic modality to combat cancer.

The following examples are given by way of illustration of the present invention and therefore should not be construed to limit the scope of the present invention.

Example 1

Synthesis of the RGD-lipopeptide 2 (Scheme 1)

Step (a): Solid HOSu (0.81 g, 7.03 mmol) and DCC (1.45 g, 7.03 mmol) were added sequentially to an ice cold and stirred solution of $N^\alpha BOC$—$N^\epsilon$—Z-L-Lysine (2.7 g, 7.03 mmol) in dry DCM (10 mL). After half an hour, N-2 amino-ethyl-N,N-di-n-hexadecylamine (I, 3.6 g, 7.03 mmol, prepared as described earlier (Majeti, B. K et al, Bioconjug Chem. 2005; 16; 676-684) and DMAP (catalytic) dissolved in dry DCM (10 mL) were added to the reaction mixture. The resulting solution was left stirred at room temperature for 16 hours, solid DCU was filtered and the solvent from the filtrate was evaporated. The residue was taken in ethyl acetate (100 mL) and washed sequentially with ice-cooled 1N HCl (1×100 mL), saturated sodium bicarbonate (1×100 mL) and water (2×100 mL). The organic layer was dried over anhydrous sodium sulfate, filtered and the solvent from the filtrate removed by rotary evaporation. The residue upon column chromatographic purification with 60-120 mesh silica gel using 12% acetone-hexane (v/v) as eluent afforded 3.7 g (60%) of the pure intermediate (II). ($R_f$=0.5 using 30% Acetone-Hexane v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.2-1.3 [bs, 52H, —(C$\underline{H}_2$)$_{13}$—]; 1.3-1.65 [m, 4H, LysC$^\gamma$$\underline{H}_2$+LysC$^\delta$$\underline{H}_2$; 9H, CO—O—C(C$\underline{H}_3$)$_3$; 4H, —N(—CH$_2$—C$\underline{H}_2$—)$_2$]; 1.7-1.8 [m, 2H, LysC$^\beta$$\underline{H}_2$]; 2.4 [t, 4H, —N(—C$\underline{H}_2$—CH$_2$—)$_2$]; 2.55 [t, 2H, —N—C$\underline{H}_2$—CH$_2$—NH—CO]; 3.1-3.4 [m, 2H, Lys$^\omega$C$\underline{H}_2$, 2H, —N—CH$_2$—C$\underline{H}_2$—NH—CO—]; 4.0 [m, 1H, LysC$^\alpha$$\underline{H}$]; 4.9-5.1 [m, 1H, N$\underline{H}$—CO—O—CH$_2$—C$_6$H$_5$; 2H, COO—C$\underline{H}_2$—C$_6$H$_5$]; 5.2 [m, 1H, LysC$^\alpha$H—N$\underline{H}$—CO—]; 6.7 [m, 1H, —CH$_2$—CH$_2$—N$\underline{H}$—CO—]; 7.1-7.3 [m, 5H, COO—CH$_2$—C$_6$$\underline{H}_5$].

LSIMS: m/z=871 [M+1]$^+$ for C$_{53}$H$_{98}$O$_5$N$_4$

Step (b): The intermediate II obtained in step (a) (3.4 g, 3.90 mmol) was dissolved in dry DCM (10 mL) and TFA (4 mL) was added at 0° C. The resulting solution was left stirred at room temperature for 5 h. to ensure complete deprotection. Excess TFA was removed by nitrogen flushing. The resulting compound was dissolved in DCM (100 mL) and triethyl amine (10 mL) was added and stirred at room temperature for 15 minutes. The solvent was completely removed by rotary evaporation. The residue was taken in DCM (100 mL) and washed with water (50 mL). The organic layer was dried over anhydrous sodium sulfate, filtered and the solvent from the filtrate removed by rotary evaporation afforded 2.76 g (91% yield). ($R_f$=0.2 using 10% Methanol-chloroform v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.1-1.6 [m, 52H, —(C$\underline{H}_2$)$_{13}$—, 4H, LysC$^\gamma$$\underline{H}_2$+LysC$^\delta$$\underline{H}_2$; 4H, —N(—CH$_2$—C$\underline{H}_2$—)$_2$]; 1.7-1.9 [m, 2H, LysC$^\beta$$\underline{H}_2$]; 2.3-2.6 [m, 4H, —N(—C$\underline{H}$—CH$_2$—)$_2$, 2H, —N—C$\underline{H}_2$—CH$_2$—NH—CO]; 3.1-3.40 [m, 2H, Lys$^\omega$C$\underline{H}_2$, 2H, —N—CH$_2$—C$\underline{H}_2$—NH—CO—, 1H, LysC$^\alpha$$\underline{H}$]; 4.8-5.0 [m, 1H, N$\underline{H}$—CO—O—CH$_2$—C$_6$H$_5$]; 5.0-5.1 [s, 2H, COO—C$\underline{H}_2$—C$_6$H$_5$]; 7.2-7.4 [m, 5H, COO—CH$_2$—C$_6$$\underline{H}_5$]; 7.6 [m, 1H, LysC$^\alpha$H—CO—N$\underline{H}$—].

Step (c): Solid HOSu (0.41 g, 3.57 mmol) and DCC (0.74 g, 3.57 mmol) were added sequentially to an ice cold and stirred solution of N-t-butyloxycarbonyl-L-Aspartic acid-β-benzylester prepared conventionally from L-Aspartic acid-β-benzyl ester (Bodanszky, M et al, the presence of peptide synthesis springer-Verlag, Berlin Heidelberg, 1984 page no: 20) (1.15 g, 3.57 mmol) in dry DCM (15 mL). After half an hour, the intermediate obtained in step b (2.75 g, 3.57 mmol) and DMAP (catalytic) dissolved in dry DCM (15 mL) were added to the reaction mixture. The resulting solution was left stirred at room temperature for 16 hours, solid DCU was filtered and the solvent from the filtrate was evaporated. The residue was taken in DCM (100 mL) and washed with water (50 mL). The organic layer was dried over anhydrous sodium sulfate, filtered and the solvent from the filtrate removed by rotary evaporation. The residue upon column chromatographic purification with 60-120 mesh silica gel using 15% acetone-hexane (v/v) as eluent afforded 2.85 g (74.2%) of the pure intermediate (III). ($R_f$=0.4 using 30% Acetone-Hexane v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.2-1.3 [bs, 52H, —(C$\underline{H}_2$)$_{13}$—]; 1.3-1.5 [m, 4H, LysC$^\gamma$$\underline{H}_2$+LysC$^\delta$$\underline{H}_2$; 9H, CO—O—C(C$\underline{H}_3$)$_3$; 4H, —N(—CH$_2$—C$\underline{H}_2$—)$_2$]; 1.7-1.8 [m, 2H, LysC$^\beta$$\underline{H}_2$]; 2.4 [t, 4H, —N(—C$\underline{H}_2$—CH$_2$—)$_2$]; 2.5 [t, 2H, —N—C$\underline{H}_2$—CH$_2$—NH—CO]; 2.6-2.8 [m, 1H, Asp C$^\beta$$\underline{H}$]; 2.95-3.05 [m, 1H, Asp C$^\beta$$\underline{H}$]; 3.1-3.3 [m, 2H, Lys$^\omega$C$\underline{H}_2$, 2H, —N—CH$_2$—C$\underline{H}_2$—NH—CO—]; 4.3 [m, 1H, LysC$^\alpha$$\underline{H}$]; 4.45 [m, 1H, AspC$^\alpha$$\underline{H}$]; 4.8-5.1 [m, 1H, N$\underline{H}$—CO—O—CH$_2$—C$_6$H$_5$; 4H, COO—C$\underline{H}_2$—C$_6$H$_5$]; 5.6 [m, 1H, BOC—N$\underline{H}$]; 6.7 [m, 1H, —CH$_2$—CH$_2$—N$\underline{H}$—CO—]; 7.1-7.3 [m, 10H, COO—CH$_2$—C$_6$$\underline{H}_5$]; 7.5 [m, 1H, LysC$^\alpha$H—N$\underline{H}$—CO].

LSIMS: m/z=1077 [M+1]$^+$ for C$_{64}$H$_{109}$O$_8$N$_5$

Step (d): The intermediate III obtained in step (c) (2.85 g, 2.65 mmol) was dissolved in dry DCM (6 mL) and TFA (3 mL) was added at 0° C. The resulting solution was left stirred at room temperature for 5 h. to ensure complete deprotection. Excess TFA was removed by nitrogen flushing. The resulting compound was dissolved in DCM (50 mL) and triethyl amine (5 mL) was added and stirred at room temperature for 15 minutes. The solvent was completely removed by rotary evaporation. The residue was taken in DCM (100 mL) and washed with water (50 mL). The organic layer was dried over anhydrous sodium sulfate, filtered and the solvent from the filtrate removed by rotary evaporation afforded 2.58 g (92% yield). ($R_f$=0.3 using 10% Methanol-chloroform v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.1-1.3 [bs, 52H, —(C$\underline{H}_2$)$_{13}$—]; 1.3-1.6 [m, 4H, LysC$^\gamma$$\underline{H}_2$+LysC$^\delta$$\underline{H}_2$]; 4H, —N(—CH$_2$—C$\underline{H}_2$—)$_2$]; 1.8-2.0 [m, 2H, LysC$^\beta$$\underline{H}_2$]; 2.3-2.6 [m, 4H, —N(—C$\underline{H}_2$—CH$_2$—)$_2$, 2H, —N—CH$_2$—CH$_2$—NH—CO]; 2.7-2.9 [m, 1H, Asp C$^\beta$$\underline{H}$; 1H, Asp C$^\beta$$\underline{H}$]; 3.1-3.35 [m, 2H, Lys$^\omega$C$\underline{H}_2$, 2H, —N—CH$_2$—C$\underline{H}_2$—NH—CO—]; 3.65 [t, 1H, AspC$^\alpha$$\underline{H}$]; 4.3 [m, 1H, LysC$^\alpha$$\underline{H}$]; 4.45 [m, 1H, AspC$^\alpha$$\underline{H}$]; 5.0-5.2 [m, 1H, N$\underline{H}$—CO—O—CH$_2$—C$_6$H$_5$, 4H, COO—C$\underline{H}_2$—C$_6$H$_5$]; 6.75 [m, 1H, —CH$_2$—CH$_2$—N$\underline{H}$—CO—]; 7.2-7.4 [m, 10H, COO—CH$_2$—C$_6$$\underline{H}_5$]; 7.9 [m, 1H, LysC$^\alpha$H—N$\underline{H}$—CO].

Step (e). N-t-butyloxycarbonyl-L-Glycine (0.43 g, 2.46 mmol) was coupled with the intermediate obtained in step (d) (2.4 g, 2.46 mmol) in presence of solid HOSu (0.51 g, 2.46 mmol), DCC (0.28 g, 2.46 mmol) and DMAP (catalytic) following essentially the same protocol as described above in step (c). The resulting crude product upon column chromatographic purification with 60-120 mesh silica gel using 30-35% acetone in petroleum ether (v/v) as eluent afforded 1.5 g (54% yield) of intermediate (IV) as a gummy solid. ($R_f$=0.45 using 35% Acetone-Hexane v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.1-1.3 [m, 52H, —(C$\underline{H}_2$)$_{13}$—]; 1.3-1.6 [m, 4H, LysC$^\gamma$$\underline{H}_2$+LysC$^\delta$$\underline{H}_2$; 9H, CO—O—C(C$\underline{H}_3$)$_3$; 4H, —N(—CH$_2$—C$\underline{H}_2$—)$_2$]; 1.8-1.9 [m, 2H, LysC$^\beta$$\underline{H}_2$]; 2.4 [t, 4H, —N(—C$\underline{H}_2$—CH$_2$—)$_2$]; 2.5 [t, 2H, —N—C$\underline{H}_2$—CH$_2$—NH—CO]; 2.6-2.9 [m, 2H, Asp C$^\beta$$\underline{H}_2$]; 3.1-3.3 [m, 2H, Lys$^\omega$C$\underline{H}_2$, 2H, —N—CH$_2$—C$\underline{H}_2$—NH—CO—]; 3.5-3.8 [m, 2H, Gly C$^\alpha$$\underline{H}_2$]; 4.2-4.4 [m, 1H, LysC$^\alpha$$\underline{H}$]; 4.7-4.9 [m, 1H, AspC$^\alpha$$\underline{H}$]; 4.95-5.1 [m, 4H, COO—C$\underline{H}_2$—C$_6$H$_5$]; 5.5-5.7 [m, 1H, BOC—N$\underline{H}$]; 6.85 [m, 1H, —CH$_2$—CH$_2$—N$\underline{H}$—CO—]; 7.2-7.3 [m, 10H, COO—CH$_2$—C$_6$$\underline{H}_5$]; 7.4-7.6 [m, 1H, LysC$^\alpha$H—N$\underline{H}$—CO; m, 1H, Gly C$^\alpha$H$_2$—N$\underline{H}$—CO].

LSIMS: m/z=1133 [M+1]$^+$ for C$_{66}$H$_{112}$O$_8$N$_6$

Step (f): The intermediate (IV) obtained in step (e) (0.7 g, 0.62 mmol) was deprotected following essentially the same protocol as described above in step (b). The resulting product upon rotary evaporation afforded 0.6 g (93% yield) of intermediate ($R_f$=0.2 using 5% Methanol-chloroform v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.1-1.3 [m, 52H, —(C$\underline{H}_2$)$_{13}$—]; 1.3-1.6 [m, 4H, LysC$^\gamma$$\underline{H}_2$+LysC$^\delta$$\underline{H}_2$; 4H, —N(—CH$_2$—C$\underline{H}_2$—)$_2$]; 1.8-1.9 [m, 2H, LysC$^\beta$$\underline{H}_2$]; 2.6-2.9 [m, 4H, —N(C$\underline{H}_2$—CH$_2$—)$_2$; 2H, —N—C$\underline{H}_2$—CH$_2$—NH—CO; 2H, Asp C$^\beta$$\underline{H}$]; 3.1-3.5 [m, 2H, Lys$^\omega$C$\underline{H}_2$, 2H, —N—CH$_2$—C$\underline{H}_2$—NH—CO—; Gly C$^\alpha$$\underline{H}_2$—N$\underline{H}_2$; Gly C$^\alpha$H$_2$—N$\underline{H}_2$]; 4.2-4.45 [m, 1H, LysC$^\alpha$$\underline{H}$]; 4.7-4.9 [m, 1H, AspC$^\alpha$$\underline{H}$]; 5.0-5.1 [m, 4H, COO—C$\underline{H}_2$—C$_6$H$_5$]; 5.85 [m, 1H, —CH$_2$—CH$_2$—N$\underline{H}$—CO—]; 7.2-7.3 [m, 10H, COO—CH$_2$—C$_6$$\underline{H}_5$]; 7.6-7.7 [m, 1H, LysC$^\alpha$H—N$\underline{H}$—CO; m, 1H, Gly C$^\alpha$H$_2$—N$\underline{H}$—CO].

Step (g). $N^\alpha$-t-butyloxycarbonyl-$N^\omega$-nitro-L-Arginine (0.18 g, 0.57 mmol) was coupled with the intermediate obtained in step (f) (0.59 g, 0.57 mmol) in presence of solid HOSu (0.066 g, 0.57 mmol), DCC (0.12 g, 0.57 mmol) and DMAP (catalytic) following essentially the same protocol as described above in step (c). The resulting crude product upon column chromatographic purification with 60-120 mesh silica gel using 5% methanol in DCM (v/v) as eluent afforded 0.35 g (46% yield) of intermediate V. ($R_f$=0.2 using 5% Methanol-chloroform v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.0-1.9 [m, 52H, —(C$\underline{H}_2$)$_{13}$—; 4H, LysC$^\gamma$$\underline{H}_2$+LysC$^\delta$$\underline{H}_2$; 9H, CO—O—C(C$\underline{H}_3$)$_3$; 4H, —N(—CH$_2$—C$\underline{H}_2$—)$_2$; Arg C$^\beta$$\underline{H}_2$+Arg C$^\gamma$$\underline{H}_2$; m, 2H, LysC$^\beta$$\underline{H}_2$]; 2.5-2.6 [m, 1H, Asp C$^\beta$$\underline{H}_1$]; 2.8-3.3 [m, 4H, —N(—C$\underline{H}_2$—CH$_2$—)$_2$; —N—C$\underline{H}_2$—CH$_2$—NH—CO; 2H, Lys$^\omega$C$\underline{H}_2$; 1H, Asp C$^\beta$$\underline{H}_2$; Arg C$^\delta$$\underline{H}_2$]; 3.4-3.7 [m, 2H, —N—CH$_2$—C$\underline{H}_2$—NH—CO—]; 3.7-4.2 [m, 2H, Gly C$^\alpha$$\underline{H}_2$; 1H, LysC$^\alpha$$\underline{H}$; 1H, Arg C$^\alpha$$\underline{H}$; 4.6-4.8 [m, 1H, AspC$^\alpha$$\underline{H}$; 4.9-5.1 [m, 4H, COO—C$\underline{H}_2$—C$_6$H$_5$]; 5.6-5.7 [m, 1H, BOC—N$\underline{H}$]; 6.1-6.3 [m, 2H, —CH$_2$—CH$_2$—N$\underline{H}$—CO—; N$\underline{H}$—COO—CH$_2$—C$_6$H$_5$]; 7.1-7.3 [m, 10H, COO—CH$_2$—C$_6$$\underline{H}_5$]; 7.6-7.9 [m, 1H, LysC$^\alpha$H—N$\underline{H}$—CO; 1H, Gly C$^\alpha$H$_2$—N$\underline{H}$—CO; 1H, Asp C$^\alpha$H—N$\underline{H}$—CO]; 8.0-8.3 [m, 3H, Guanidine N$\underline{H}$—CN—N$\underline{H}_2$]

LSIMS: m/z=1335 [M+1]$^+$ for C$_{72}$H$_{123}$O$_{12}$N$_{11}$.

Steps (h,i,j): The intermediate obtained in step (g) (0.1 g, 0.075 mmol) was dissolved in dry DCM (2 mL) and TFA (0.5 mL) was added at 0° C. The resulting solution was left stirred at room temperature for 5 h. to ensure complete deprotection. Excess TFA was removed by nitrogen flushing. The resulting compound was dissolved in methanol (3 mL) and 10% Pd/C was added to it. The reaction mixture was stirred at room temperature for 20 h in presence of hydrogen gas. The reaction mixture was then diluted with methanol (50 mL) and the catalyst was filtered through celite. Solvent was rotary evaporated followed by chloride ion exchange chromatography (using Amberlyst A-26 chloride ion exchange resin) and crystallization in acetone afforded 0.037 g (50% yield) of the pure target lipid 2 ($R_f$=0.10 using 35% Methanol-chloroform v/v, as the TLC developing solvent).

$^1$H NMR (400 MHz, CDCl$_3$+CD$_3$OD): δ/ppm=0.9 [t, 6H, C$\underline{H}_3$—(CH$_2$)$_{15}$—]; 1.0-2.2 [m, 52H, —(C$\underline{H}_2$)$_{13}$—; 4H, LysC$^\gamma$$\underline{H}_2$+LysC$^\delta$$\underline{H}_2$; 4H, —N(CH$_2$—C$\underline{H}_2$—)$_2$; Arg C$^\beta$$\underline{H}_2$+Arg C$^\gamma$$\underline{H}_2$; m, 2H, LysC$^\beta$$\underline{H}_2$]; 2.6-3.3 [m, 1H, Asp C$^\beta$$\underline{H}_1$; 4H, —N(—C$\underline{H}_2$—CH$_2$—)$_2$; 2H, —N—C$\underline{H}_2$—CH$_2$—NH—CO; 2H, Lys$^\omega$C$\underline{H}_2$; 1H, Asp C$^\beta$$\underline{H}_2$]; 3.4-4.8 [m, 2H, —N—CH$_2$—C$\underline{H}_2$NH—CO—; 2H, Gly C$^\alpha$$\underline{H}_2$; Arg C$^\delta$H2; 1H, LysC$^\alpha$$\underline{H}$; 1H, Arg C$^\alpha$$\underline{H}$; 1H, AspC$^\alpha$$\underline{H}$+CD$_3$O$\underline{D}$].

LSIMS: m/z=966 [M+1]$^+$ for C$_{51}$H$_{105}$O$_6$N$_{10}$

Example 2

Synthesis of the RGE-Lipopeptide 3 (Representative Control Non-Integrin Binding Lipopeptide Counterpart of the Integrin-Binding RGD-Lipopeptide 2)

Step (a): Solid HOBt (0.488 g, 3.62 mmol) and EDCI (0.693 g, 3.62 mmol) were added sequentially to an ice cold and stirred solution of $N^\alpha$BOC—$N^\epsilon$—Z-L-Lysine (1.15 g, 3.62 mmol) in dry DCM (10 mL). After half an hour, N-2 aminoethyl-N,N-di-n-hexadecylamine (I, 1.67 g, 3.28 mmol, prepared as described earlier (Majeti, B. K et al, *Bioconjug Chem.* 2005; 16; 676-684) dissolved in dry DCM (10 mL) were added to the reaction mixture. The resulting solution was left stirred at room temperature for 16 hours. The solution was taken in chloroform (50 mL) and washed sequentially with ice-cooled 1N HCl (2×100 mL), saturated sodium bicarbonate (2×100 mL) and brine (1×100 mL). The organic layer was dried over anhydrous sodium sulfate, filtered and the solvent from the filtrate removed by rotary evaporation. The residue upon column chromatographic purification with 60-120 mesh silica gel using 12% acetone-hexane (v/v) as eluent afforded 1.72 g (60%) of the pure intermediate (II). ($R_f$=0.5 using 30% Acetone-Hexane v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.2-1.3 [bs, 52H, —(C$\underline{H}_2$)$_{13}$—]; 1.3-1.65 [m, 4H, LysC$^\gamma$$\underline{H}_2$+LysC$^\delta$$\underline{H}_2$; 9H, CO—O—C(C$\underline{H}_3$)$_3$; 4H, —N(—CH$_2$—C$\underline{H}_2$—)$_2$]; 1.7-1.8 [m; 2H, LysC$^\beta$$\underline{H}_2$]; 2.4 [t, 4H, —N(—C$\underline{H}_2$—CH$_2$—)$_2$]; 2.55 [t, 2H, —N—C$\underline{H}_2$—CH$_2$—NH—CO]; 3.1-3.4 [m, 2H, Lys$^\omega$CH$_2$, 2H, —N—CH$_2$—CH$_2$—NH—CO—]; 4.0 [m, 1H, LysC$^\alpha$$\underline{H}$]; 4.9-5.2 [m, 1H, N$\underline{H}$—CO—O—CH$_2$—C$_6$H$_5$; 2H, COO—C$\underline{H}_2$—C$_6$H$_5$; m, 1$\underline{H}$, LysC$^\alpha$H—N$\underline{H}$—CO—]; 6.7 [m, 1H, —CH$_2$—CH$_2$—N$\underline{H}$—CO—]; 7.1-7.3 [m, 5H, COO—CH$_2$—C$_6$$\underline{H}_5$].

LSIMS: m/z=871 [M+1]$^+$ for C$_{53}$H$_{98}$O$_5$N$_4$

Step (b): The intermediate II obtained in step (a) (0.85 g, 0.98 mmol) was dissolved in dry DCM (10 mL) and TFA (4 mL) was added at 0° C. The resulting solution was left stirred at room temperature for 5 h. to ensure complete deprotection. Excess TFA was removed by nitrogen flushing. The resulting compound was dissolved in DCM (100 mL) and triethyl amine (10 mL) was added and stirred at room temperature for 15 minutes. The solvent was completely removed by rotary evaporation. The residue was taken in DCM (100 mL) and washed with water (50 mL). The organic layer was dried over anhydrous sodium sulfate, filtered and the solvent from the filtrate removed by rotary evaporation afforded 0.708 g (94% yield). ($R_f$=0.2 using 10% Methanol-chloroform v/v, as the TLC developing solvent).

Step (c): Solid HoBt (0.188 g, 1.38 mmol) and EDCI (0.264 g, 1.38 mmol) were added sequentially to an ice cold and stirred solution of N-t-butyloxycarbonyl-L-Glutamic acid-β-benzylester prepared conventionally from L-Glutamic acid-β-benzyl ester ((0.464 g, 1.38 mmol) in dry DCM (15 mL). After half an hour, the intermediate obtained in step b (0.708 g, 0.92 mmol) dissolved in dry DCM (15 mL) were added to the reaction mixture. The resulting solution was left stirred at room temperature for 16 hours. The solution was taken in chloroform (50 mL) and washed sequentially with ice-cooled 1N HCl (2×100 mL), saturated sodium bicarbonate (2×100 mL) and brine (1×100 mL). The organic layer was dried over anhydrous sodium sulfate, filtered and the solvent from the filtrate removed by rotary evaporation. The residue upon column chromatographic purification with 60-120 mesh silica gel using 15% acetone-hexane (v/v) as eluent afforded 0.7 g (70%) of the pure intermediate (III). ($R_f$=0.4 using 30% Acetone-Hexane v/v, as the TLC developing solvent).

$^1$H NMR (300 MHz, CDCl$_3$): δ/ppm=0.9 [t, 6H, CH$_3$—(CH$_2$)$_{15}$—]; 1.2-1.3 [bs, 52H, —(C$\underline{H}_2$)$_{13}$—]; 1.3-1.5 [m, 4H, LysC$^\gamma$$\underline{H}_2$+LysC$^\delta$$\underline{H}_2$; 9H, CO—O—C(C$\underline{H}_3$)$_3$; 4H, —N(—CH$_2$—C$\underline{H}_2$—)$_2$]; 1.7-2.2 [m, 2H, LysC$^\beta$$\underline{H}_2$; 2H, Glu C$^\beta$$\underline{H}_2$]; 2.5 [m, 4H, —N(C$\underline{H}_2$—CH$_2$—)$_2$, 2H, Glu C$^\gamma$$\underline{H}_2$]; 2.6 [t, 2H, —N—C$\underline{H}_2$—CH$_2$—NH—CO]; 3.2-3.4 [m, 2H, Lys$^\omega$C$\underline{H}_2$, 2H, —N—CH$_2$—C$\underline{H}_2$—NH—CO—]; 4.15 [m, 1H, LysC$^\alpha$$\underline{H}$]; 4.35 [m, 1$\underline{H}$, GluC$^\alpha$$\underline{H}$]; 5.0-5.2 [m, 1H, N$\underline{H}$—CO—O—CH$_2$—C$_6$H$_5$; 4H, COO—C$\underline{H}_2$—C$_6$H$_5$]; 5.4 [m, 1H, BOC—N$\underline{H}$]; 6.8-7.2 [m, 1H, —CH$_2$—CH$_2$—N$\underline{H}$—CO—; m, 1$\underline{H}$, LysC$^\alpha$H—N$\underline{H}$—CO]; 7.3 [m, 10H, COO—CH$_2$—C$_6$$\underline{H}_5$]

LSIMS: m/z=1091 [M+1]$^+$ for C$_{65}$H$_{111}$O$_8$N$_5$

Step (d): The intermediate III obtained in step (c) (0.7 g, 0.64 mmol) was dissolved in dry DCM (6 mL) and TFA (3 mL) was added at 0° C. The resulting solution was left stirred at room temperature for 5 h. to ensure complete deprotection. Excess TFA was removed by nitrogen flushing. The resulting compound was dissolved in DCM (50 mL) and triethyl amine (5 mL) was added and stirred at room temperature for 15 minutes. The solvent was completely removed by rotary evaporation. The residue was taken in DCM (100 mL) and washed with water (50 mL). The organic layer was dried over anhydrous sodium sulfate, filtered and the solvent from the filtrate removed by rotary evaporation afforded 0.6 g (94% yield). ($R_f$=0.3 using 10% Methanol-chloroform v/v, as the TLC developing solvent).

Step (e). N-t-butyloxycarbonyl-L-Glycine (0.318 g, 1.82 mmol) was coupled with the intermediate obtained in step (d) (0.6 g, 0.61 mmol) in presence of solid HOBt (0.246 g, 1.82 mmol), EDCI (0.348 g, 1.82 mmol)) following essentially the same protocol as described above in step (c). The resulting crude product upon column chromatographic purification with 60-120 mesh silica gel using 30-35% acetone in petroleum ether (v/v) as eluent afforded 0.382 g (55% yield) of intermediate (IV) as a gummy solid. ($R_f$=0.45 using 35% Acetone-Hexane v/v, as the TLC developing solvent).

$^1$H NMR (300 MHz, CDCl$_3$): δ/ppm=0.9 [t, 6H, C$\underline{H}_3$—(CH$_2$)$_{15}$—]; 1.2-1.3 [bs, 52H, —(C$\underline{H}_2$)$_{13}$—]; 1.3-1.5 [m, 4H, LysC$^\gamma$$\underline{H}_2$+LysC$^\delta$$\underline{H}_2$]; 9H, CO—O—C(C$\underline{H}_3$)$_3$; 4H, —N(—CH$_2$—C$\underline{H}_2$—)$_2$]; 1.7-2.2 [m, 2H, LysC$^\beta$$\underline{H}_2$; 2H, Glu C$^\beta$$\underline{H}_2$]; 2.5 [m, 4H, —N(—C$\underline{H}_2$—CH$_2$—)$_2$; 2H, Glu C$^\gamma$$\underline{H}_2$]; 2.6 [t, 2H, —N—C$\underline{H}_2$—CH$_2$—NH—CO]; 3.2-3.4 [m, 2H, Lys$^\omega$C$\underline{H}_2$, 2H, —N—CH$_2$—C$\underline{H}_2$—NH—CO—]; 4.15 [m, 1H, LysC$^\alpha$$\underline{H}$]; 4.35 [m, 1H, GluC$^\alpha$$\underline{H}$; 2H, GlyC$^\alpha$$\underline{H}_2$]; 5.0-5.2 [m, 1H, N$\underline{H}$—CO—O—CH$_2$—C$_6$H$_5$; 4H, COO—C$\underline{H}_2$—C$_6$H$_5$]; 5.8 [m, 1H, BOC—N$\underline{H}$]; 7.3 [m, 10H, COO—CH$_2$—C$_6$$\underline{H}_5$] 7.4-7.9 [m, 1H, —CH$_2$—CH$_2$—N$\underline{H}$—CO—; m, 1H, LysC$^\alpha$H—N$\underline{H}$—CO; m, 1H, GluC$^\alpha$H—N$\underline{H}$—CO—];

LSIMS: m/z=1147 [M+1]$^+$ for C$_{67}$H$_{114}$O$_8$N$_6$

Step (f): The intermediate (IV) obtained in step (e) (0.382 g, 0.33 mmol) was deprotected following essentially the same protocol as described above in step (b). The resulting product upon rotary evaporation afforded 0.32 g (92% yield) of intermediate ($R_f$=0.2 using 5% Methanol-chloroform v/v, as the TLC developing solvent).

Step (g). N$^\alpha$-t-butyloxycarbonyl-N$^\omega$-nitro-L-Arginine (0.093 g, 0.29 mmol) was coupled with the intermediate obtained in step (f) (0.24 g, 0.25 mmol) in presence of solid HoBt (0.039 g, 0.29 mmol), EDCI (0.056 g, 0.29 mmol) following essentially the same protocol as described above in step (c). The resulting crude product upon column chromatographic purification with 60-120 mesh silica gel using 5% methanol in DCM (v/v) as eluent afforded 0.16 g (50% yield) of intermediate V. ($R_f$=0.2 using 5% Methanol-chloroform v/v, as the TLC developing solvent).

$^1$H NMR (300 MHz, CDCl$_3$): δ/ppm=0.9 [t, 6H, CH$_3$—(CH$_2$)$_{15}$—]; 1.2-2.0 [bs, 52H, —(C$\underline{H}_2$)$_{13}$—; m, 4H, LysC$^\gamma$$\underline{H}_2$+LysC$^\delta$$\underline{H}_2$; 9H, CO—O—C(C$\underline{H}_3$)$_3$; 4H, —N(—C$\underline{H}_2$—CH—)$_2$; 2H, Glu C$^\beta$$\underline{H}_2$; 2H, LysC$^\gamma$$\underline{H}_2$]; 2.1-2.6 [m, 4H, —N(C$\underline{H}_2$—CH$_2$—)$_2$; m, 2H, —N—C$\underline{H}_2$—CH$_2$—NH—CO; 2H, LysC$^{\beta H}_2$; 2H Arg C$^\beta$$\underline{H}_2$; 2H, Glu C$^\gamma$$\underline{H}_2$]; 3.0-3.4 [m, 2H, Lys$^\omega$C$\underline{H}_2$, 2H, —N—CH$_2$—C$\underline{H}_2$—NH—CO—; 2H, Arg C$^\delta$$\underline{H}_2$]; 3.9-4.3 [m, 1H, LysC$^\alpha$$\underline{H}$; m, 1H, GluC$^\alpha$$\underline{H}$; 2H, GlyC$^\alpha$$\underline{H}_2$]; 5.0-5.2 [m, 1H, N$\underline{H}$—CO—O—CH$_2$—C$_6$H$_5$; 4H, COO—C$\underline{H}_2$—C$_6$H$_5$]; 5.8 [m, 1H, BOC—N$\underline{H}$]; 7.3 [m, 10H, CO—CH$_2$—C$_6$$\underline{H}_5$] 7.4-7.9 [m, 1H, —CH$_2$—CH$_2$—N$\underline{H}$—CO—; m, 1H, LysC$^\alpha$H—N$\underline{H}$—CO; m, 1H, GluC$^\alpha$H—N$\underline{H}$—CO—; 1H, Gly C$^\alpha$H$_2$—N$\underline{H}$—CO];

LSIMS: m/z=1349 [M+1]$^+$ for C$_{72}$H$_{123}$O$_{12}$N$_{11}$.

Steps (h,i,j): The intermediate obtained in step (g) (0.1 g, 0.075 mmol) was dissolved in dry DCM (2 mL) and TFA (0.5 mL) was added at 0° C. The resulting solution was left stirred at room temperature for 5 h. to ensure complete deprotection. Excess TFA was removed by nitrogen flushing. The resulting compound was dissolved in methanol (3 mL) and 10% Pd/C was added to it. The reaction mixture was stirred at room temperature for 20 h in presence of hydrogen gas. The reaction mixture was then diluted with methanol (50 mL) and the catalyst was filtered through celite. Solvent was rotary evaporated followed by chloride ion exchange chromatography (using Amberlyst A-26 chloride ion exchange resin) and crystallization in acetone afforded 0.037 g (50% yield) of the pure target lipid 3 ($R_f$=0.10 using 35% Methanol-chloroform v/v, as the TLC developing solvent).

$^1$H NMR (400 MHz, CDCl$_3$+CD$_3$OD): δ/ppm=0.9 [t, 6H, C$\underline{H}_3$—(CH$_2$)$_{15}$—]; 1.0-2.2 [m, 52H, —(C$\underline{H}_2$)$_{13}$—; 4H, LysC$^\gamma$$\underline{H}_2$+LysC$^\delta$$\underline{H}_2$; 4H, —N(C$\underline{H}_2$—CH$_2$—)$_2$; Arg C$^\beta$$\underline{H}_2$+Arg C$^\gamma$$\underline{H}_2$; m, 2H, LysC$^\beta$$\underline{H}_2$]; 2.6-3.3 [m, 2H, Glu C$^\gamma$$\underline{H}_2$; 4H, —N(—C$\underline{H}_2$—CH$_2$—)$_2$; 2H, —N—C$\underline{H}_2$—CH$_2$—NH—CO; 2H, Lys$^\omega$C$\underline{H}_2$; m, 2H, Glu C$^\beta$$\underline{H}_2$]; 3.4-4.8 [m, 2H, —N—CH$_2$—C$\underline{H}_2$—NH—CO—; 2H, Gly C$^\alpha$$\underline{H}_2$; Arg C$^\delta$$\underline{H}$2; 1H, LysC$^\alpha$$\underline{H}$, Arg C$^\alpha$$\underline{H}$; 1H, GluC$^\alpha$$\underline{H}$+CD$_3$OD], LSIMS: m/z=980 [M+1]$^+$ for C$_{51}$H$_{105}$O$_6$N$_{10}$ Example 3

Evaluation of the In Vitro Gene Transfer Efficacies

Cells were seeded at a density of 20000 cells per well in a 96-well plate 18-24 hours before the transfection. 0.3 μg of plasmid DNA was complexed with varying amounts of RGD-lipopeptides (0.45-7.2 nmol) in plain DMEM medium (total volume made up to 100 μL) for 30 minutes. The lipopeptide: DNA charge ratios (+/−) were varied from 0.3:1 to 9:1. The RGD-lipopeptide:DNA complexes were then added to the cells. After 4 h of incubation, 100 μL of DMEM with 20% FBS was added to the cells. The medium was changed to 10% complete medium after 24 h and the reporter gene activity was estimated after 48 h. The cells were washed twice with PBS (100 μl each) and lysed in 50 μl lysis buffer [0.25 M Tris-HCl pH 8.0, 0.5% NP40]. Care was taken to ensure complete lysis. The β-galactosidase activity per well was estimated by adding 50 μl of 2×-substrate solution [1.33 mg/ml of ONPG, 0.2 M sodium phosphate (pH 7.3) and 2 mM magnesium chloride] to the lysate in a 96-well plate. Absorbance at 405 nm was converted to β-galactosidase units using a calibration curve constructed with pure commercial β-galactosidase enzyme. The values of β-galactosidase units in triplicate experiments assayed on the same day varied by less than 20%.

For transfection experiments using cells pretreated with commercially available integrin antagonists (e.g. cyclic RGDfV and linear RGDS, FIG. 3, Part A), cells were pre-incubated with the diluted integrin antagonists (using 150 μM final concentration of antagonists). In case of transfection experiments using L27 cells pre-incubated with commercially available monoclonal antibodies of α$_5$β$_1$, α$_v$β$_3$ and α$_v$β$_5$ integrin receptors, cells were pretreated using 25 times diluted (v/v) monoclonal antibodies.

The transfection experiment was carried in triplicate and the transfection efficiency values shown in FIG. 1A are the average of triplicate experiments performed on the same day. Each transfection experiment was repeated two times and the day to day variation in average transfection efficiency was found to be within 2-fold. The transfection profiles obtained on different days were identical.

Example 4

Transfection Assay by the Whole Cell Histochemical X-Gal Staining of Transfected L27 and CHO Cells Transfected L27 and CHO Cells expressing β-galactosidase were histochemically stained with the substrate 5-bromo-4-chloro-3-indolyl-β-D-galactopyranoside (X-gal), as described previously (Majeti, B. K. et al 2005). Forty eight hours after transfection with RGD-lipopeptide: DNA complexes in 96 well plates, the cells were washed two times (2×100 μL) with phosphate-buffered saline (PBS, 137 mM NaCl, 2.7 mM KCl, 10 mM Na$_2$HPO$_4$, 2 mM KH$_2$PO$_4$, pH 7.4) and fixed with 0.5% glutaraldehyde in PBS (225 μL). After 15 minutes incubation at room temperature, the cells were washed again with PBS three times (3×250 μL) and subsequently, were stained with 1.0 mg/mL X-gal in PBS containing 5.0 mM $K_3[Fe(CN)_6]$, and 5.0 mM $K_4[Fe(CN)_6]$ and 1 mM $MgSO_4$ for 2-4 hours at 37° C. Blue colored cells were identified by light microscope (Leica, Germany). FIG. 2 shows the histochemical whole cell X-gal staining of the transfected L27 and CHO cells with A at lipopeptide:DNA charge ratios at 9:1. X-gal staining results summarized in FIG. 2 convincingly demonstrate that the gene transfer efficacies of the RGD-lipopeptide A in L27 cells with over expressed integrins is remarkably superior to that in CHO cells lacking significant amount of surface integrins.

Example 5

Percent Cell Viabilities

Cytotoxicities of the lipopeptide A were evaluated by the 3-(4,5-dimethylthiazol-2-yl)-2,5-diphenyltetrazolium bromide (MTT) reduction assay both in combination with DOPE and Cholesterol. The assay was performed in 96-well plates by maintaining the same ratio of number of cells to amount of A as used in the transfection experiments. MTT was added 3 h after addition of A to the cells. Results were expressed as percent viability=[$A_{540}$(treated cells)-background/$A_{540}$(untreated cells)-background]×100.

Advantages of the Invention

1. Integrin binding RGD lipopeptides are useful as gene transfer reagents.
2. RGD lipopeptides are useful for delivering polyanions, polypeptides or nucleopolymers into cells.
3. RGD lipopeptide can be formulated with therapeutic agents including anticancer agent.

We claim:
1. A $\alpha_5\beta_1$ integrin receptor specific RGD-lipopeptide having the generic structure A

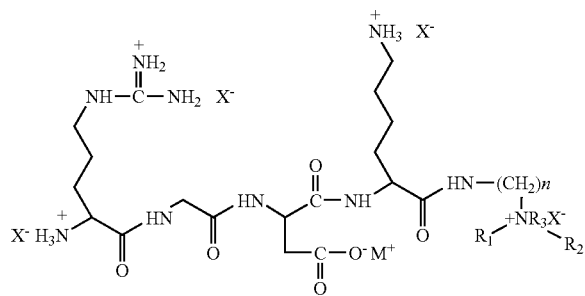

A wherein:
each of $R_1$ and $R_2$ is independently hydrogen or a lipophilic moiety, provided both $R_1$ and $R_2$ are not hydrogen simultaneously, the lipophilic moiety being selected from group consisting of alkyl group, mono-unsaturated alkenyl group, di-unsaturated alkenyl group and tri-unsaturated alkenyl group, each of which having at least eight carbon atoms;

$R^3$ is selected from group consisting of hydrogen, straight chain alkyl group having 1 to 5 carbon atoms, and branched alkyl chain alkyl group having 1 to 5 carbon atoms;

n is an integer having value between 1 and 7;

and X is optionally a halogen moiety; and

M is selected from the group consisting of hydrogen, sodium and potassium.

2. The RGD-lipopeptide as claimed in claim 1, wherein the lipophilic moiety contains 8-22 carbon atoms.

3. The RGD-lipopeptide as claimed in claim 1, wherein X is chlorine, bromine or iodine.

4. The RGD-lipopeptide as claimed in claim 1, wherein each of $R_1$ and $R_2$ is independently hydrogen or an aliphatic hydrocarbon chain, provided both $R_1$ and $R_2$ are not hydrogen simultaneously.

5. The RGD-lipopeptide as claimed in claim 1, wherein both $R_1$ and $R_2$ are aliphatic hydrocarbon chains.

6. The RGD-lipopeptide as claimed in claim 1, wherein $R_3$ is an alkyl group and both $R_1$ and $R_2$ are aliphatic hydrocarbon chains.

7. The RGD-lipopeptide as claimed in claim 1, wherein $R_3$ is a hydrogen atom and both $R_1$ and $R_2$ are aliphatic hydrocarbon chains.

8. The RGD-lipopeptide as claimed in claim 1, wherein $R_3$ is an alkyl group and $R_1$ and $R_2$ are independently hydrogen or an aliphatic hydrocarbon chain.

9. The RGD-lipopeptide as claimed in claim 1, wherein each one of $R_1$ and $R_2$ groups containing about 8-22 carbon atoms is independently alkyl group containing 8-22 carbon atoms or a mono-, di- or tri-unsaturated alkenyl group containing 8-22 carbon atoms.

10. The RGD-lipopeptide as claimed in claim 9, wherein each R1 and $R_2$ group contains about 16 to about 22 carbon atoms.

11. The RGD-lipopeptide as claimed in claim 9 or 10, wherein $R_1$ and $R_2$ is independently a mono-unsaturated alkenyl group.

12. The RGD-lipopeptide as claimed in claim 1, wherein both $R_1$ and $R_2$ are the same and saturated alkyl group having 12 to 18 carbon atoms.

13. The RGD-lipopeptide of claim 1, wherein both $R_1$ and $R_2$ are the same and are mono-unsaturated alkenyl group having 18 to 22 carbon atoms.

\* \* \* \* \*